(12) United States Patent
Winsor et al.

(10) Patent No.: US 7,085,430 B2
(45) Date of Patent: Aug. 1, 2006

(54) CORRECTING GEOMETRIC DISTORTION IN A DIGITALLY CAPTURED IMAGE

(75) Inventors: Robin Winsor, Calgary (CA); Arunas Salkauskas, Calgary (CA)

(73) Assignee: Imaging Dynamics Company Ltd., Calgary (CA)

( * ) Notice: Subject to any disclaimer, the term of this patent is extended or adjusted under 35 U.S.C. 154(b) by 779 days.

(21) Appl. No.: 10/302,822

(22) Filed: Nov. 25, 2002

(65) Prior Publication Data

US 2003/0118227 A1 Jun. 26, 2003

Related U.S. Application Data

(60) Provisional application No. 60/333,224, filed on Nov. 23, 2001, provisional application No. 60/333,252, filed on Nov. 23, 2001, provisional application No. 60/333,207, filed on Nov. 23, 2001, provisional application No. 60/333,206, filed on Nov. 23, 2001.

(51) Int. Cl.
*G06K 9/40* (2006.01)
(52) U.S. Cl. ........................ 382/275; 382/132
(58) Field of Classification Search ................ 382/275, 382/210, 132; 324/309; 600/414; 430/22
See application file for complete search history.

(56) References Cited

U.S. PATENT DOCUMENTS

| | | | | |
|---|---|---|---|---|
| 5,005,578 A | * | 4/1991 | Greer et al. | 600/414 |
| 5,795,687 A | * | 8/1998 | Yasuda | 430/22 |
| 5,940,537 A | * | 8/1999 | Regen et al. | 382/210 |
| 6,445,182 B1 | * | 9/2002 | Dean et al. | 324/309 |
| 6,606,421 B1 | * | 8/2003 | Shaked et al. | 382/275 |
| 6,694,047 B1 | * | 2/2004 | Farrokhnia et al. | 382/132 |

* cited by examiner

*Primary Examiner*—Sanjiv Shah
(74) *Attorney, Agent, or Firm*—Gowling Lafleur Henderson LLP; D. Doak Horne

(57) ABSTRACT

The present invention is directed generally to correcting geometric distortion in a digitally captured image. The method involves receiving an uncorrected digital image of a phantom having a plurality of fiduciary marks; locating an uncorrected digital position for each of the fiduciary marks; mapping the uncorrected digital position to a corrected digital position for each fiduciary mark; and interpolating or extrapolating the fiduciary mark map to all pixels in the uncorrected digital image, thereby creating a correction map for uncorrected digital images.

14 Claims, 5 Drawing Sheets

24  26

CORRECTING GEOMETRIC DISTORTION IN A DIGITALLY CAPTURED IMAGE

RELATED APPLICATIONS

This application claims priority from and incorporates by reference U.S. application No. 60/333,224 entitled "Lens Assembly and Barrel Correction Method For X-Ray System", U.S. application No. 60/333,252 entitled "Self Diagnostic System for Optically Coupled Digital Radiography", U.S. application No. 60/333,207 entitled "Positioning Stand for a Radiography Imaging Device", and U.S. application No. 60/333,206 entitled "Balancing Areas of Varying Density in a Digital Image", all filed on Nov. 23, 2001.

FIELD OF THE INVENTION

The present invention relates generally to digital imaging, and in particular to correcting for geometric distortion in digital image caused by a lens assembly used in capturing the image.

BACKGROUND OF THE INVENTION

For over one hundred years photographic films have been used to capture and display X-rays for diagnostic purposes. In the last ten years or so, digital radiography has become increasingly popular. Digital radiography refers to the application of digital image processing techniques to projection radiography (x-rays). Digitally recorded x-rays are superior to those recorded with photographic film due to the greater dynamic range of the digital recording system. Furthermore, computer image processing techniques provide a wealth of capabilities to study otherwise obscured details within the image.

To take a digital radiograph, a digital radiography imaging unit is positioned behind a subject. A standard radiographic generator directs radiation through the subject to a fluorescent-imaging screen mounted just behind the front surface of the imaging unit. The imaging screen is the conversion media for radiation to visible light. The fluorescent-imaging screen absorbs the radiographic radiation and emits light of a particular wavelength which closely matches the peak sensitivity of a charge coupled device (CCD) camera. A front-surfaced mirror is positioned at a 45 degree angle inside the imaging unit to direct the radiographic image into the CCD) camera. The mirror allows the CCD camera to be positioned out of the direct path of the radiation, effectively shielding it from radiation exposure and prolonging its life. A high-efficiency lens reduces the image and directs it onto the surface of the CCD.

The visual image formed by the fluorescent-imaging screen is converted into a digital image by the CCD sensor. A control computer converts the image into a medical image file that can be viewed for clinical diagnosis, enhanced and electronically stored with the patient demographic information in a picture archiving system.

In the digital x-ray imaging unit described above, it is desired to place the lens as close as possible to the fluorescent screen in order to capture as much light as possible. In so doing, the required dose of radiation to the patient is reduced. However, such positioning of the lens requires the lens to have a very wide angle and be very fast, i.e. have a large aperture. When an image is taken using such a lens, distortions are typically introduced into the image. Also, distortions can appear in other digital imaging applications, especially where the lenses used have a wide angle and/or have a large aperture. While such distortions do not represent a loss of data, but rather the misplacing of it, it is desirable to view a distortion-free image.

SUMMARY OF THE INVENTION

In producing a distortion free image, it is desirable to avoid introducing structured noise patterns which, even at very low levels, the human eye can sometimes discern and which may be boosted by subsequent image processing procedures. It is therefore an objective of the invention to correct a distorted image and prevent the appearance of structured noise due to said correction.

According to one aspect of the invention, there is provided a method for correcting geometric distortion in a digitally captured image. The method comprises the following steps:
(a) receiving an uncorrected digital image of a phantom having a plurality of fiduciary marks;
(b) locating an uncorrected position for each of the fiduciary marks;
(c) mapping the uncorrected position to a corrected position for each fiduciary mark by
   (i) designating a fiduciary mark near the center of the digital image as the central fiduciary mark;
   (ii) determining the correct distance between adjacent fiduciary marks
   (iii) creating a digital map of the corrected position of each fiduciary mark by locating the positions relative to the central fiduciary mark that are multiples of the correct distance;
   (iv) associating the uncorrected position of each fiduciary mark with the closest corrected position until one of the fiduciary marks is more than a selected distance from a corrected position, then predicting the correct position of next fiduciary mark and then associating the predicted correct position with the closest correct position; and
(d) interpolating or extrapolating the fiduciary mark mapping over all pixels in the uncorrected digital image, thereby creating a correction map for uncorrected digital images.

The correct distance may be determined by averaging the distance of uncorrected fiduciary marks closest to the central fiduciary position.

The phantom may comprise a plurality of fiduciary marks arranged in a rectangular array. In particular, the fiduciary marks may be substantially identical circular holes arranged in a square grid pattern. The use of holes in a flat radio-opaque material is superior to the use of radio-opaque objects, such as steel balls, as it provides a square wave cross section of x-ray intensity. Balls, by contrast, would provide a Gaussian x-ray intensity cross section. The square wave is superior for use in this method as it allows for more distinct separation between the fiduciary point and the background intensity.

One way to locate the uncorrected position of the fiduciary marks is by
(i) obtaining a flat field reference digital image;
(ii) obtaining a shade-corrected phantom image by multiplying the uncorrected digital image of the phantom by the reciprocal of the flat field reference image;
(iii) identifying pixels in the shade-corrected phantom image that are higher than a selected threshold intensity as being potential fiduciary marks;
(iv) calculating the area and dimensions of each of the potential fiduciary marks and identify the potential fiduciary marks within a selected area and dimension range as being uncorrected fiduciary marks; and (v) locating the geometric centers of the uncorrected fiduciary marks.

The threshold intensity may be selected as the average of the phantom image intensity.

DETAILED DESCRIPTION

Figure 1:
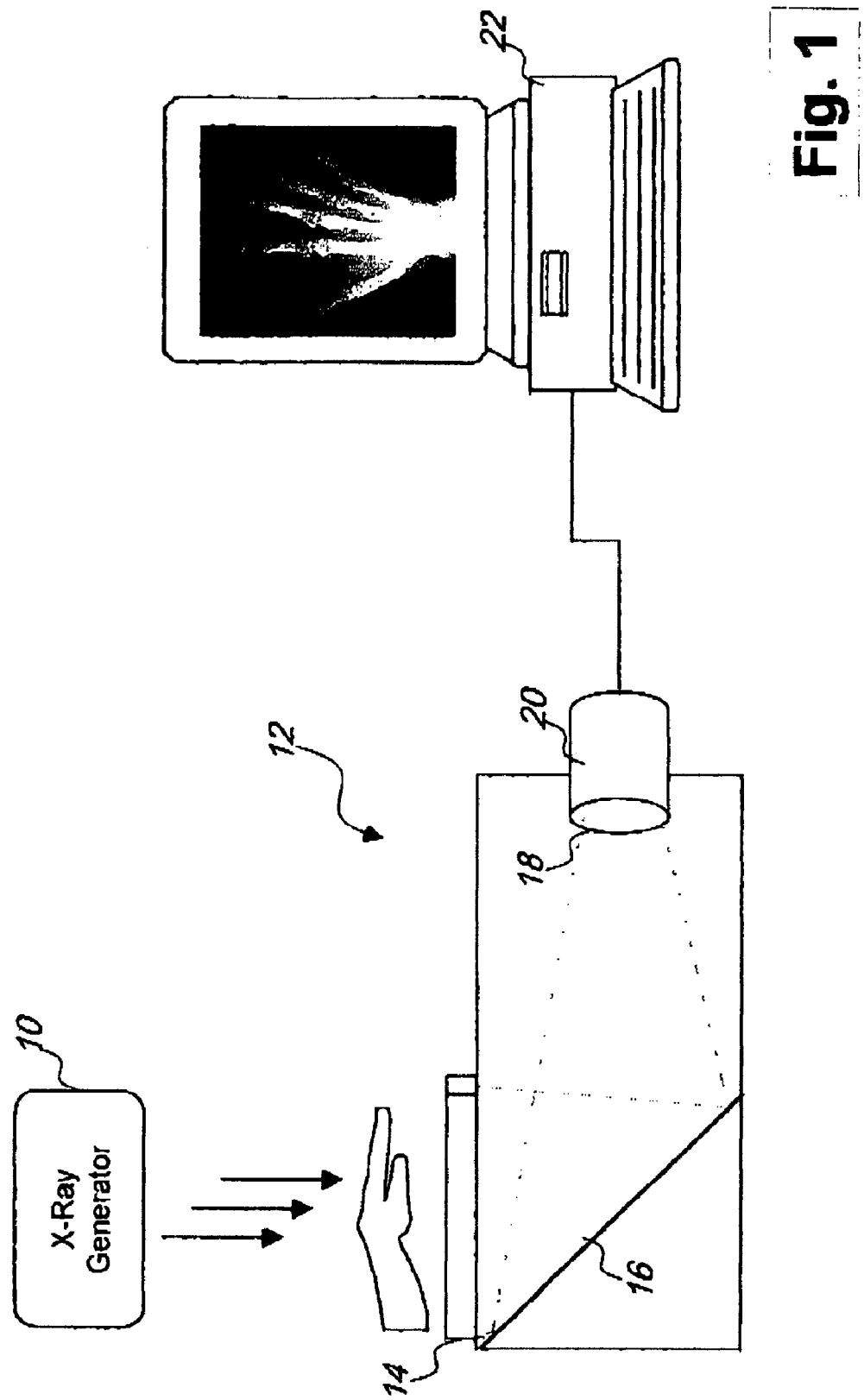
FIG. 1 is a schematic illustration of a digital radiography system having a detector with a lens assembly and charge coupled device (CCD) camera.

Referring to FIG. 1, an x-ray imaging system is provided for taking digital x-ray images of a subject, such as a patient for medical diagnostic purposes. As soon as a patient is in position and a part of the patient's body selected for imaging has been set in place, an x-ray source 10 is turned on and x-rays are directed towards the patient. X-rays passing through the patient are captured by a detector 12 and converted into a digital x-ray image. In particular, the x-ray image reaching the detector 12 is first converted into visible light by a scintillator 14. The visible light is then reflected by a mirror 16 towards lenses in a lens assembly 18, which reduces and directs the visual image onto the surface of a charge-coupled device (CCD) 20, which converts the visual image into a digital image.

Known systems have made use of optical methods to reduce the image for x-ray imaging for up to 4 million pixels, but recent high resolution systems use many more pixels; for example, the Xplorer 1700 manufactured by Imaging Dynamics Company Ltd. uses 16 million pixels. With only 4 million pixels the limiting resolution is 2.5 line pairs per millimeter. With 16 million the limiting resolution is closer to 5 line pairs and requires a correspondingly better performance from the lens.

The lenses in lens assembly 18 enables a high resolution system to operate at reduced radiation levels and higher resolution. This means a better quality image and the potential to diagnose medical problems at an earlier stage than would be possible with other systems.

After the digital image has been reduced by the lens assembly 18 and captured by the CCD 20, the digital image is then transferred to a computer 22 which is communicatively linked to the CCD 20. The computer 22 stores the captured raw (unprocessed) digital image in a medical image file, and runs an imaging processing program to process the raw image data into an enhanced form more useful for viewing.

The imaging processing program employs a series of imaging enhancing methods that are applied to enhance the appearance of the captured raw image. First a dark field correction method is applied to correct for image noise caused by current generated by the thermal processes within the CCD. This is an additive process. Then, a flat field correction method is employed for correcting for a flat field map of pixel non-uniformity (some pixels will respond to light with a higher output than others). This is a multiplicative process.

Then, a geometric correction method is employed for correcting distortion caused by the design of the lens assembly 18. When an image is taken with the lens assembly 18, distortions are introduced into the image. As discussed above, the lens assembly 18 is placed as close as possible to the fluorescent screen 14 in order to capture as much light as possible. In so doing, the required dose of radiation to the patient is reduced. Such positioning requires the lens assembly 18 to have a wide angle and fast lens, i.e. a large aperture. This combination means that barrel distortion, in which the sides of the image appear to bow outwards, is quite pronounced. Recognizing that barrel distortion does not represent a loss of data, but the misplacing of it, the geometric correction method applies an appropriate inverse distortion to the distorted image to remove the distortion. The geometric correction method may also be applied to correct an image that has been inadvertently rotated, caused for example, by a camera that is not perfectly aligned with a subject.

Generally speaking, the geometric correction method creates a correction map between a distorted position and an undistorted position for each pixel in a digital image of a calibration phantom taken by a digital camera. This correction map can be applied to all digital images taken by the camera, to correct the position of any distorted pixels.

A phantom is a simple target used in x-ray imaging to produce many of the characteristics of an optical distortion target. In optical wavelength imaging, distortion is corrected by imaging a target with black dots on a white background, or vice versa, and then finding the distortion. This approach does not work well for x-ray imaging as it is difficult to produce an image with pure black and white detail. The x-ray beam will at least partly penetrate any material unless it is very thick lead or a similar material with high atomic number.

Figure 2:
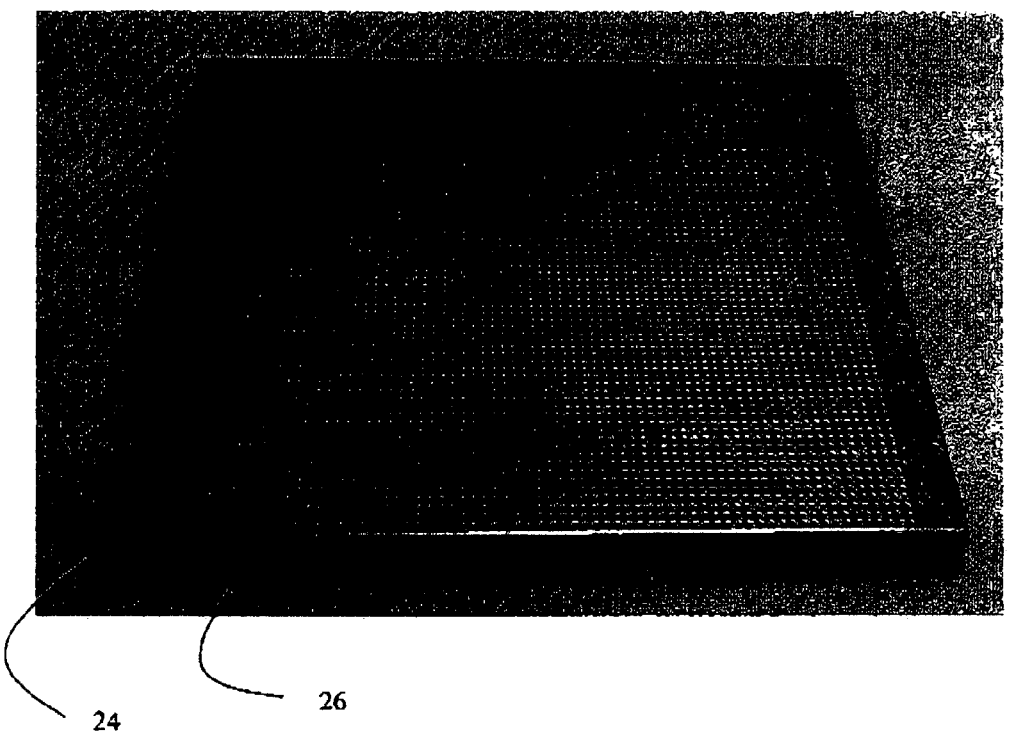
FIG. 2 is an oblique view of an x-ray calibration phantom having a square array of fiduciary holes.

Therefore, according to an embodiment of the invention and referring to FIG. 2, an x-ray phantom 24 is provided having a sheet of stainless steel with holes 26. ⅛" in diameter, and spaced ¼" apart center to center. The 4761 holes are arranged in a square array of 69×69 covering an area of 17"×17" as measured from the center of the outermost holes 26. The holes 26 serve as fiduciary marks that are used by the geometric correction method to create a correction map.

The exact size, shape and number of holes 26 are selectable by the operator. The particular number in this embodiment was chosen for ease of manufacturing and calibration resolution. Fewer holes will result in poorer resolution in the correction map, and more holes will increase the burden on the processor.

Figure 4:
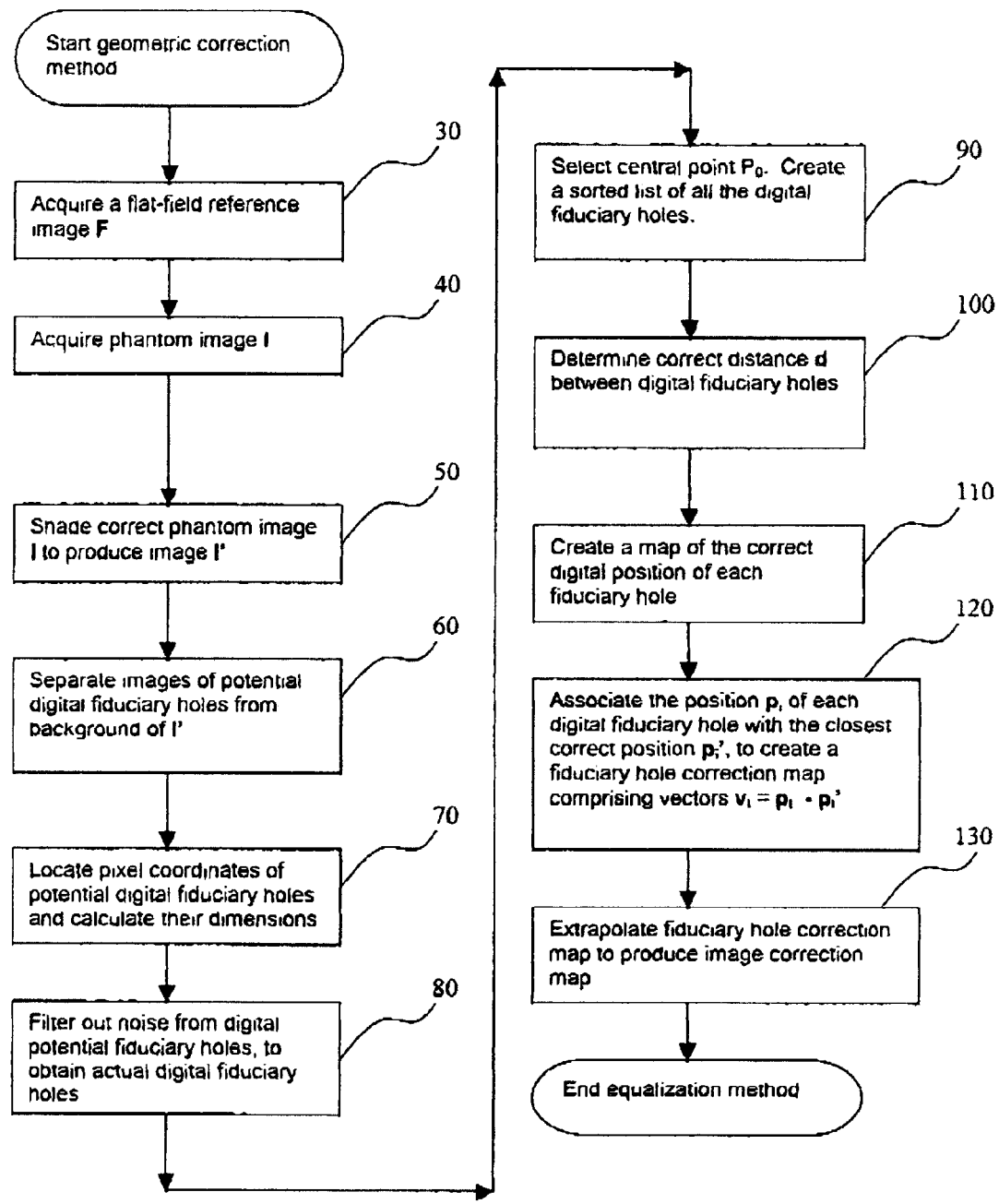
FIG. 4 is a flow chart of a geometric correction method for correcting distortion in an uncorrected digital image taken by the digital radiography system.

The geometric correction method as described below relies on the fact that the holes 26 have known "correct" positions; although it is not necessary for the holes 26 to be positioned in a square array in the phantom 24, such positioning simplifies the correction process. Using the x-ray imaging system, the steps carried out in the correction method are shown in the flow chart in FIG. 4 and are described below:

1) Acquire an uncorrected digital image without the phantom 26; this image will be used as a flat-field reference image F (shown as process block 30 in FIG. 4).

Figure 3:
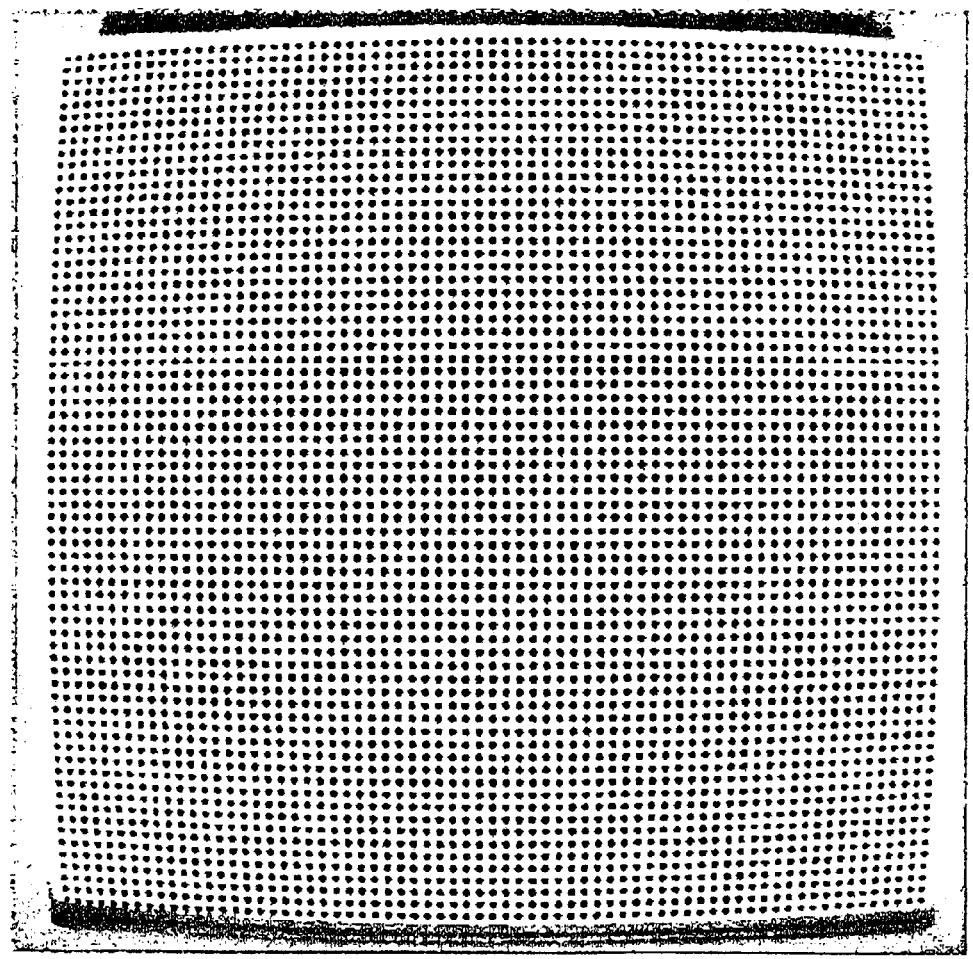
FIG. 3 is an uncorrected digital image of the calibration phantom taken by the digital radiography system.

2) Acquire an image with the phantom I (as shown in FIG. 3 and in process block 40 in FIG. 4).

3) Shade-correct the phantom image I by scaling the pixel values in I by the reciprocals of the corresponding pixels in the flat-field reference image F to produce shade-corrected phantom image I' (shown as process block 50 in FIG. 4). Such shade correction is desired to compensate for a non-uniform "bowing" of intensity in the image, caused by certain physical properties of the imaging equipment; for example, lenses in the lens assembly 18 tend to gather more light near its center, and the x-ray source 10 tends to project more x-rays towards the center of the image than the periphery.

4) Compute the average intensity of the pixels in shade-corrected phantom image I'. As the digital fiduciary holes will have a higher intensity than the background, use this average as a threshold to separate the images of potential digital fiduciary holes from the background (shown as process block 60 in FIG. 4). The threshold value can be manually selected or adjusted by the operator.

5) Locate the pixel coordinates of the images of the digital potential fiduciary holes and compute their dimensions, areas and geometric centers (shown as process block 70 in FIG. 4).

6) Filter out noise from digital potential fiduciary holes, thereby identifying the digital fiduciary holes, by discarding any potential fiduciary mark that does not fall within a selected dimensional criteria (shown as process block 80 in FIG. 4). This dimensional criteria includes an area and size range that is based on the actual (physical) area and size of the fiduciary holes 26. Such discarded noise can be caused, for example, by stray x-rays impacting the CCD 20.

7) Select a digital fiduciary hole near the center of the image and designate the geometric center of this hole as the central point $P_0$. The method assumes this point $P_0$ has a minimal amount of distortion in the digital image. Create a sorted list of all the digital fiduciary holes; the sorting is based on the distance and angle relative to the central point $P_0$ (shown as process block 90 in FIG. 4).

8) Compute the average distance d between the central point $P_0$ and the geometric center of the closest four neighbouring fiduciary holes (as the holes are arranged in a square array, these four points describe a square rotated by 45 degrees). d is assumed to be the correct distance between all the points and their nearest neighbours (as shown in process block 100 in FIG. 4).

9) Starting at the central point $p_0$, create a map of the correct digital position of each fiduciary holes (shown as process block 110 in FIG. 4). This is accomplished by creating a list of points whose coordinates are multiples of d.

10) Associate the position $p_i$ of each digital fiduciary hole with the closest correct position $p_i'$, to create a fiduciary hole correction map comprising vectors $v_i = p_i - p_i'$ that describe the offset required to move each digital fiduciary hole from the distorted position $p_i$ to the corrected position $p_i'$ (as shown in process block 120 in FIG. 4). This is a non trivial procedure if there is significant distortion, i.e., when the method reaches fiduciary holes near the edges of the digital image. Therefore, the method includes a prediction subroutine: where the distance between the position $p_i$ of the digital fiduciary hole and the nearest correct position $p_i'$ exceeds a certain threshold, e.g. 20%, the remaining associations will first predict the correct location $p_{p[i]}$ of the digital fiduciary hole $p_i$ by interpolating from the correction vectors of the previously associated and neighbouring fiduciary holes. Then, the method will locate the nearest correct position from the predicted correct location $p_{p[i]}$ of the fiduciary hole.

11) Extrapolate the fiduciary hole correction map to every pixel in the digital image, to provide a digital image correction map (as shown in process block 130 in FIG. 4). The fiduciary hole correction map is comprised of two small images X and Y, 69×69 pixels each, wherein each pixel represents the respective X and Y coordinate of the corrected position $p_i'$. and the respective coordinates of $p_i$ are placed into those pixels. The X and Y images are enlarged by standard resampling techniques to size of the digital image I, thereby producing a map for corrected image I'.

Figure 5:
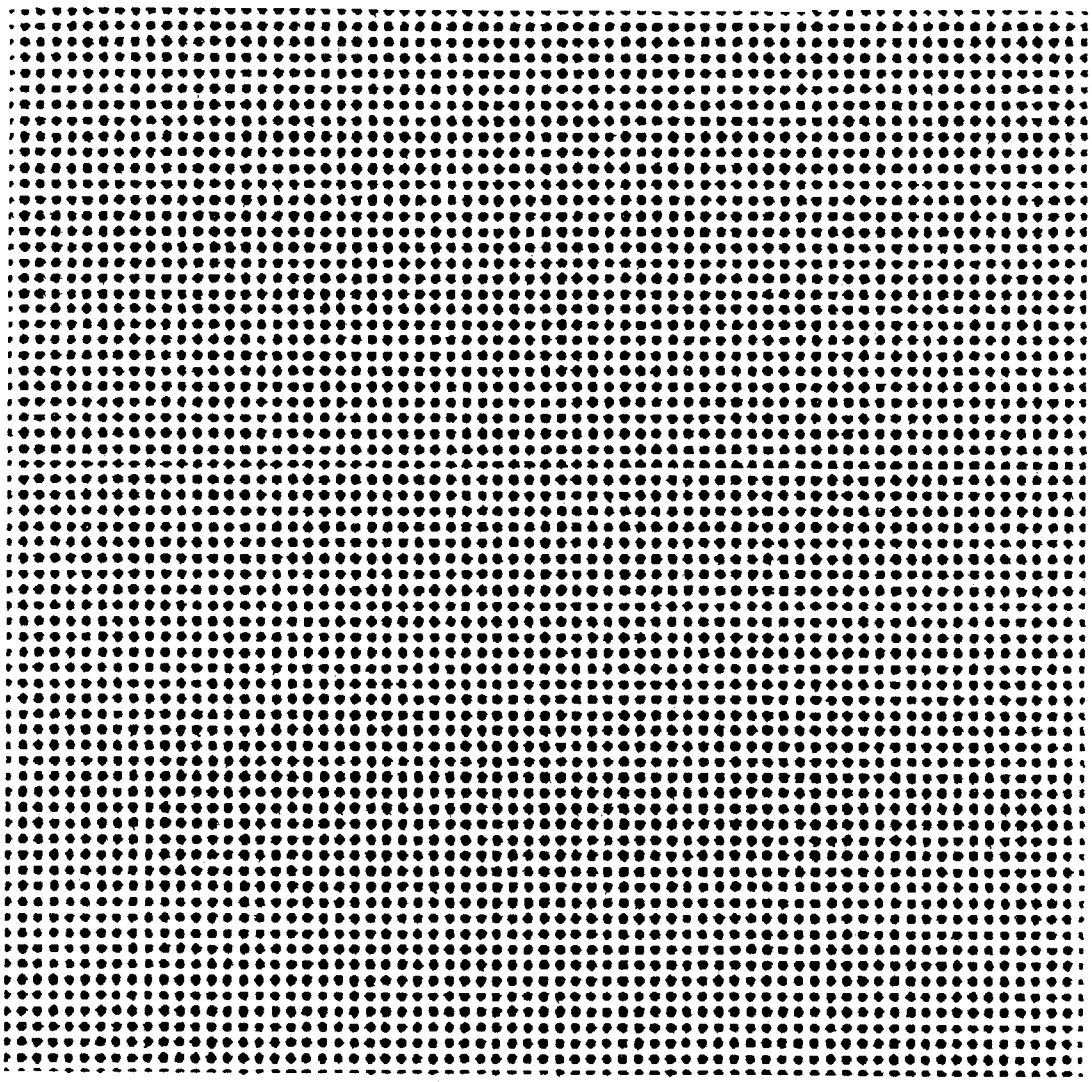
FIG. 5 is a corrected digital image as corrected by the geometric correction method.

That is, X and Y now describe, for each pixel in the corrected image I' where in I to retrieve a value from. X and Y are images with floating-point values, so evaluating $I'(i,j) = I[X(i,j), Y(i,j)]$ will typically require interpolation between pixels. This is performed using readily available commercial software, for example, the Intel image processing library. The corrected image I' is shown in FIG. 5.

As described above, correction for geometric distortion in a digital image involves resampling the image in a manner that can result in fixed patterns appearing in subtle details of the corrected image. These arise because for some pixels the resampling coincides precisely with a pixel in the distorted image, and for other pixels the resampling falls in between pixels in the distorted image. The result is alternating bands of sharp looking pixels and bands of blurry looking pixels.

The blurring is not substantial, but the difference between the bands is readily apparent and is especially noticeable after any image enhancements are applied.

In a further refinement to the method, this problem is solved by breaking up the patterns by adding small amounts of noise to the distortion correction.

The typical corrected image is determined by: $I'[i,j] = I[X[i,j], Y[i,j]]$, where X and Y are maps from the corrected image coordinates to the distorted image coordinates. We add noise to the maps X and Y by randomly perturbing their values by Gaussian noise with a mean of 0 and a standard deviation of 0.5.

Variations include linking the standard deviation to the amount by which $(X[i,j], Y[i,j])$ differs from the nearest pair of integers $(X'[i,j], Y'[i,j])$—the difference is measured as the Pythagorean distance d between the two points $(X[i,j], Y[i,j])$ and $(X'[i,j], Y'[i,j])$. This difference never exceeds the square-root of 0.5, which is approximately 0.707. We therefore use the 0.708−d as the standard deviation for the noise function. The result is that wherever $(X[i,j], Y[i,j])$ coincides very strongly with an existing pixel, we specifically nudge it away so that the image is blurred uniformly.

Some variations are possible, for example, X and Y can be rotated to affect a rotation in I', this is the ideal way of performing 90 degree rotations. As well, since small rotations can affect a loss of resolution in I' we may choose to rotate the points $p_i$ by a corrective amount before creating X and Y. We compute an estimate of the angle by computing the average of the angles between $p_i - p_0$ and $p_i' - p_0'$. The rotation is performed relative to $p_0$.

The geometric correction method is encoded as a module in a program that is part of the x-ray imaging system. After the system has taken the raw digital image and applied the geometric correction to the image, the system executes a segmentation algorithm to determine which part of the body is being imaged. Then, the program applies an automatic contrast enhancement (the selected enhancement values depending on the part of the body), by mapping the 4000+ shades of gray captured by the CCD into the 256 shades available for display on the computer monitor. Then, a conventional digital unsharp masking method is applied to sharpen certain aspects of the captured image. Then, an equalization process is applied to balance out the image in the manner described above. Finally, the processed image may be sent to a display device for viewing.

While the preferred embodiment of the invention has been illustrated and described, it will be appreciated that various changes can be made therein without departing from the scope and spirit of the invention

What is claimed is:

1. A method for correcting geometric distortion in a digitally captured image, comprising:
   (a) receiving an uncorrected digital image of a phantom having a plurality of fiduciary marks;
   (b) locating an uncorrected position for each of the fiduciary marks;
   (c) mapping the uncorrected position to a corrected position for each fiduciary mark by
      (i) designating a fiduciary mark near the center of the digital image as the central fiduciary mark;
      (ii) determining the correct distance between adjacent fiduciary marks
      (iii) creating a digital map of the corrected position of each fiduciary mark by locating the positions relative to the central fiduciary mark that are multiples of the correct distance;
      (iv) associating the uncorrected position of each fiduciary mark with the closest corrected position until one of the fiduciary marks is more than a selected distance from a corrected position, then predicting the correct position of next fiduciary mark and then associating the predicted correct position with the closest correct position; and
   (d) interpolating or extrapolating the fiduciary mark mapping over all pixels in the uncorrected digital image, thereby creating a correction map for uncorrected digital images.

2. The method of claim 1 wherein the correct distance is determined by averaging the distance of uncorrected fiduciary marks closest to the central fiduciary position.

3. The method of claim 2 wherein the phantom comprises a plurality of fiduciary marks in a rectangular array.

4. The method of claim 3 wherein the phantom is made from a metal sheet, and the fiduciary marks are substantially identically sized circular holes in the sheet and arranged in a square array.

5. The method of claim 1 wherein in (b) the uncorrected position of the fiduciary marks are located by
   (i) obtaining a flat field reference digital image;
   (ii) obtaining a shade corrected phantom image by multiplying the uncorrected digital image of the phantom by the reciprocal of the flat field reference image;
   (iii) identifying pixels in the shade-corrected phantom image that are higher than a selected threshold intensity as being potential fiduciary marks;
   (iv) calculating the area and dimensions of each of the potential fiduciary marks and identify the potential fiduciary marks within a selected area and dimension range as being uncorrected fiduciary marks; and
   (v) locating the geometric centers of the uncorrected fiduciary marks.

6. The method of claim 5 wherein the threshold intensity is selected as the average of the phantom image intensity.

7. The method of claim 1 further comprising adding noise to a corrected image corrected by the correction map, by randomly perturbing the values in the corrected image by Gaussian noise by a selected value.

8. A computer-readable medium encoded with a program module for correcting geometric distortion in a digitally captured image by:
   (a) receiving an uncorrected digital image of a phantom having a plurality of fiduciary marks;
   (b) locating an uncorrected position for each of the fiduciary marks;
   (c) mapping the uncorrected position to a corrected position for each fiduciary mark by
      (i) designating a fiduciary mark near the center of the digital image as the central fiduciary mark;
      (ii) determining the correct distance between adjacent fiduciary marks
      (iii) creating a digital map of the corrected position of each fiduciary mark by locating the positions relative to the central fiduciary mark that are multiples of the correct distance;
      (iv) associating the uncorrected position of each fiduciary mark with the closest corrected position until one of the fiduciary marks is more than a selected distance from a corrected position, then predicting the correct position of next fiduciary mark and then associating the predicted correct position with the closest correct position; and
   (d) interpolating or extrapolating the fiduciary mark mapping over all pixels in the uncorrected digital image, thereby creating a correction map for uncorrected digital images.

9. The computer-readable medium of claim 8 wherein the correct distance is determined by averaging the distance of uncorrected fiduciary marks closest to the central fiduciary position.

10. The computer-readable medium of claim 9 wherein the phantom comprises a plurality of fiduciary marks in a rectangular array.

11. The method of claim 10 wherein the phantom is made from a metal sheet, and the fiduciary marks are substantially identically sized circular holes in the sheet and arranged in a square array.

12. The computer-readable medium of claim 8 wherein in (b) the uncorrected position of the fiduciary marks are located by
   (i) obtaining a flat field reference digital image;
   (ii) obtaining a shade corrected phantom image by multiplying the uncorrected digital image of the phantom by the reciprocal of the flat field reference image;
   (iii) identifying pixels in the shade-corrected phantom image that are higher than a selected threshold intensity as being potential fiduciary marks;
   (iv) calculating the area and dimensions of each of the potential fiduciary marks and identify the potential fiduciary marks within a selected area and dimension range as being uncorrected fiduciary marks; and
   (v) locating the geometric centers of the uncorrected fiduciary marks.

13. The computer-readable medium of claim 12 wherein the threshold intensity is selected as the average of the phantom image intensity.

14. The computer readable medium of claim 8 further comprising a module for adding noise to a corrected image corrected by the correction map, by randomly perturbing the values in the corrected image by Gaussian noise by a selected value.

* * * * *